(12) United States Patent
Weber (10) Patent No.: US 7,074,412 B2
(45) Date of Patent: Jul. 11, 2006

(54) PHARMACEUTICAL COMPOSITION

(75) Inventor: Franz Weber, Singen (DE)

(73) Assignee: The University of Zurich, Zurich (CH)

( * ) Notice: Subject to any disclaimer, the term of this patent is extended or adjusted under 35 U.S.C. 154(b) by 0 days.

(21) Appl. No.: 10/354,856

(22) Filed: Jan. 30, 2003

(65) Prior Publication Data

US 2004/0152627 A1    Aug. 5, 2004

(51) Int. Cl.
- A61K 39/00 (2006.01)
- A61K 38/00 (2006.01)
- A61K 47/30 (2006.01)
- A61F 2/00 (2006.01)

(52) U.S. Cl. .................. 424/198.1; 424/426; 424/428; 514/772.3; 514/12; 523/115

(58) Field of Classification Search ................ 530/350, 530/399; 514/2; 424/78.22; 548/534
See application file for complete search history.

(56) References Cited

U.S. PATENT DOCUMENTS

| | | | |
|---|---|---|---|
| 5,324,519 A | 6/1994 | Dunn et al. | ................ 424/426 |
| 2003/0022828 A1* | 1/2003 | Akella et al. | ................. 514/12 |
| 2003/0104029 A1 | 6/2003 | Pirhonen et al. | ............ 424/426 |
| 2003/0105530 A1 | 6/2003 | Pirhonen et al. | ......... 623/23.72 |

FOREIGN PATENT DOCUMENTS

| | | |
|---|---|---|
| EP | 0 433 225 A1 | 6/1991 |
| EP | 0 560 014 | 9/1993 |
| EP | 1 126 822 | 8/2001 |
| WO | WO 03/060076 | 7/2003 |

OTHER PUBLICATIONS

Andriano, K., et al. J. Biomed. Mat. Res. (Appl. Biomater.) 2000, vol. 53, pp. 36-43.*
Li, R., and J. Wozney. Trends in Biotech. 2001, vol. 19(7), pp. 255-265.*
Daluiski et al., Nature Genetics, 2001, vol. 27, pp. 84-88.*
Wolfam et al., J. Clin Invest. 1997, vol. 100, pp. 321-330.*
Bodine et al., "Development and Characterization of a Conditionally Transformed Adult Human Osteoblastic Cell Line," *J. Bone Mineral Res.*, 11:806-819 (1996).
Dahlin et al., "Membrane-Induced Bone Augmentation at Titanium Implants," *Int. J. Periodontics Rest. Dent.*, 11(4):273-281 (1991).
Hämmerle and Karring, "Guided bone regeneration at oral implant sites," *Peridontol. 2000*, 17:151-175 (1998).
Israel et al., "Expression and Characterization of Bone Morphogenetic Protein-2 in Chinese Hamster Ovary Cells," *Growth Factors*, 7:139-150 (1992).
Johnson et al., "Distal Metaphyseal Tibial Nonunion," *Clin. Orthop.*, 250:234-240 (1990).
Katagiri et al., "The Non-Osteogenic Mouse Pluripotent Cell Line, C3H10T1/2, Is Induced to Differentiate into Osteoblastic Cells by Recombinant Human Bone Morphogenetic Protein-2," *Biochem. Biophys. Res. Com.*, 172:295-300 (1990).
Klinge et al., "Osseous Response to Implanted Natural Bone Mineral and Synthetic Hydroxylapatite Ceramic in the Repair of Experimental Skull Bone Defects," *J. Oral Maxillofac. Surg*, 50:241-249 (1992).
Lowry et al., "The Quantitative Histochemistry of Brain," *J. Biol. Chem.*, 207:19-37 (1954).
Nyman and Lang, "Guided tissue regeneration and dental implants," *Periodontol. 2000*, 4:109-118 (1994).
Reddi, "Bone Morphogenetic Proteins: an Unconventional Approach to Isolation of First Mammalian Morphogens," *Cytokine & Growth Factor Review*, 8:11-20 (1997).
Rose and Oreffo, "Bone Tissue Engineering: Hope vs Hype," *R.O.C. Biochem. Biophys. Res. Com.*, 292:1-7 (2002).
Ruppert et al., "Human bone morphogenetic protein 2 contains a heparin-binding site which modifies its biological activity," *Eur. J. Biochem.*,237:295-302 (1996).
Suzawa et al., "Extracellular Matrix-Associated Bone Morphogenic Proteins Are Essential for Differentiation of Murine Osteoblastic Cells *in Vitro,"Endocrin*, 140(5):2125-2133 (1999).
Weber et al., "Disulfide Bridge Conformers of Mature BMP Are Inhibitors for Heterotopic Ossification," *Biochem. Biophys. Res. Commun.*, 286:554-558 (2001).
Weber et al., "Slow and continuous application of human recombinant bone morphogenetic protein via biodegradable poly(lactide-co-glycolide) foamspheres," *Int. J. Oral Maxilofac. Surg.*, 31:60-65 (2002).
Wozney and Rosen, "Bone Morphogenetic Protein and Bone Morphogenetic Protein Gene Family in Bone Formation and Repair," *Clin. Orthop. Rel. Res*, 346:26-37 (1998).
Wozney et al., "Novel Regulators of Bone Formation: . . . ," *Science*, 242:1528-1534 (1988).
*The Biomedical Engineering Handbook*, Ed. J.D. Bronzino, CRC Press, Boca Raton, FL, Chapter 41, pp. 1-22 (2000).
Bartsch et al., "Acute Toxicity of Various Solvents in the Mouse and Rat," *Drug Res.*, 26(8):1581-1583 (1976).
Wozney "Bone Morphogenetic Proteins," *Progress in Growth Factor Research*, 1:267-280 (1989).

* cited by examiner

*Primary Examiner*—David S. Romeo
*Assistant Examiner*—Daniel C. Garnett
(74) *Attorney, Agent, or Firm*—Banner & Witcoff, Ltd.

(57) ABSTRACT

The present invention relates to pharmaceutical compositions containing a synergistic amount of at least one bone morphogenetic protein (BMP) and a synergistic amount of at least one pyrrolidone optionally in a pharmaceutically acceptable carrier, such as a biodegradable polymer. The present invention further relates to methods of treating orthopaedic and dental, including periodontal, diseases by simultaneously administering a synergistic amount of at least one bone morphogenetic protein (BMP) and a synergistic amount of at least one pyrrolidone optionally in a pharmaceutically acceptable carrier to patients in need of such treatment.

25 Claims, 4 Drawing Sheets

SEQUENCE LISTING

```
<160> NUMBER OF SEQ ID NOS: 1

<210> SEQ ID NO 1
<211> LENGTH: 381
<212> TYPE: DNA
<213> ORGANISM: Homo sapiens

<400> SEQUENCE: 1
atgcaagcca aacacaaaca gcggaaacgc cttaagtcca gctgtaagag acaccctttg      60
tacgtggact tcagtgacgt ggggtggaat gactggattg tggctccccc ggggtatcac     120
gccttttact gccacggaga atgccctttt cctctggctg atcatctgaa ctccactaat     180
catgccattg ttcagacgtt ggtcaactct gttaactcta agattcctaa ggcatgctgt     240
gtcccgacag aactcagtgc tatctcgatg ctgtaccttg acgagaatga aaaggttgta     300
ttaaagaact atcaggacat ggttgtggag ggttgtgggt gtcgctagta cagcaaaatt     360
aaatacataa atatatatat a                                               381
```

PHARMACEUTICAL COMPOSITION

BACKGROUND OF THE INVENTION

1. Field of the Invention

The present invention relates to pharmaceutical compositions containing a synergistic amount of at least one bone morphogenetic protein (BMP) and a synergistic amount of at least one pyrrolidone optionally in a pharmaceutically acceptable carrier, such as a biodegradable polymer. The present invention further relates to methods of treating orthopaedic and dental, including periodontal, diseases by simultaneously administering a synergistic amount of at least one bone morphogenetic protein (BMP) and a synergistic amount of at least one pyrrolidone optionally in a pharmaceutically acceptable carrier to patients in need of such treatment.

2. Description of the Related Art

In the last decade guided bone regeneration (GBR) has been introduced as a predictable and effective method for enhancing bone healing, and in particular in conjunction with the placement of dental implants GBR is a clinically well-documented and successful procedure [Dahlin, C., et al., Int J Periodontics Restorative Dent 11 (1991) 273–281; Hämmerle, C. H. and Karring, T., Periodontol 2000 17 (1998) 151–175; Nyman, S. R. and Lang, N. P. Periodontol 2000 4 (1994) 109–118]. In GBR, a membrane serves as a barrier for the connective tissue and maintains an open space for the time bone needs to fill it up.

An acceleration of this bone filling process can be achieved by the principle of osteoconduction, if the empty space is filled with porous materials, which serve as a scaffold for the newly formed bone [Reddi, H., Cytokine & Growth Factor Reviews 8 (1997) 11–20]. Alternatively, bone repair can be accelerated by osteoinduction, which involves the application of appropriate growth factors capable to differentiate mesenchymal stem cells to osteoblasts [Wozney, J. M. and Rosen, V., Clin Orthop Rel Res 346 (1998) 26–37].

The most useful growth factors in osteoinduction are bone morphogenetic proteins (BMPs), which are differentiation factors and have been isolated based on their ability to induce bone formation [Wozney, J. M., et al., Science 242 (1988) 1528–1534]. They build the BMP-family with more than thirty members belonging to the TGF-β-super-family. The BMP-family is divided to subfamilies including the BMPs, such as BMP-2 and BMP-4, osteogenic proteins (Ops), such as OP-1 or BMP-7, OP-2 or BMP-8, BMP-5, BMP-6 or Vgr-1, cartilage-derived morphogenetic proteins (CDMPs), such as CDMP-1 or BMP-14 or GDF-5, growth/differentiation factors (GDFs), such as GDF-1, GDF-3, GDF-8, GDF-9, GDF-11 or BMP-11, GDF-12 and GDF-14, and other subfamilies, such as BMP-3 or osteogenin, BMP-9 or GDF-2, and BMP10 (Reddi et al., 1997, supra).

Especially in animal models the BMPs have proved to be powerful inducers of bone formation and repair. However, due to the instant degradation of the BMPs upon contact with body fluids and the strong morphogenetic action of the BMPs, un-physiologically high doses of the BMPs are needed for the osteoinductive bioactivity [Weber, F. E., et al., Int J Oral Maxillofac Surg 31 (2002) 60–65; Rose, F. R. A. and Oreffo, R. O. C. Biochem Biophys Res Com 292 (2002) 1–7]. Topical administration routes must be used, which makes the choice of the carrier system critical, and suitable carrier systems are currently not available. Since the BMPs are usually produced with recombinant techniques and thus are expensive and available only in limited amounts, the BMPs, despite the acknowledged effect, have had no impact on the medical treatment of patients and they are not clinically applied at present.

Biodegradable (also referred to as resorbable, absorbable, and erodible) polymers are at present the material of choice for controlled-release systems, including those implantable into the patients to be treated due to their transient foreign-body reactions and their ability to regenerate tissues (see, for instance, The Biomedical Engineering Handbook, Bronzino, J. D., Ed., CRC Press, Boca Raton, 2000, chapter 41, pages 41–1 to 41–22). The most studied biodegradable polymers include poly(lactic acid)s (PLA), poly(lactide-co-glycolide)-poly(ethyleneglycol) (PLG-PEG) copolymers, PLG-PGA copolymers, and like. However, synthetic biodegradable polymers are rigid and lack the flexibility needed to be applicable for instance in GBR, especially in dental GBR.

In U.S. patent application Ser. No. 10/006,800 the Applicants disclose that the rigidity of biodegradable polymers can be softened and their flexibility increased by a treatment with a known plastiziser, N-methyl-2-pyrrolidone (NMP), to an extent that allows their use in GBR. Additionally, it was found that NMP itself had an unexpected bone formation inducing effect.

New approaches in the utilization of the BMPs as well as in the application of biodegradable polymers as carriers in medicine are still needed.

The object of the present invention is to meet this need and provide new means to overcome the disadvantages and the drawbacks described above.

An object of the present invention is thus to provide novel means for the utilization of the bone forming inductive activity of the BMPs in the treatment of patients in dentistry, including periodontics, and in other fields in medicine, such as orthopedics.

Another object of the invention is to provide means, which afford a dose reduction of the BMPs, especially recombinantly produced BMPs, thereby allowing a safe and cost effective use of the BMPs in the treatment of patients in dentistry, including periodontics, and in other fields in medicine, such as orthopedics.

Still a further object of the invention is to provide new means for the use of guided bone regeneration (GBR).

Yet another object of the invention is to provide new means for the use of biodegradable membranes in GBR, whereby the second surgical stage can be avoided.

An object of the present invention is to provide pharmaceutical compositions, in which the bone morphogenetic properties of the BMPs together with the bone formation inducing properties of pyrrolidones, such as NMP, are utilized in synergistic manner, the compositions being useful in the treatment of dental and periodontal diseases, including the integration of dental implants and the filling of tooth sockets following extraction.

A further object of the present invention is to provide pharmaceutical compositions, in which the bone morphogenetic properties of the BMP together with the bone formation inducing properties of pyrrolidones, such as NMP, and biodegradable polymers are utilized in a synergistic manner, the compositions being useful in the treatment of dental and periodontal diseases, including the integration of dental implants and the filling of tooth sockets following extraction, specifically via guided bone regeneration (GBR).

Yet a further object of the present invention is to provide a method of treating a subject in a need of induction of bone formation, in which the bone morphogenetic properties of the BMP together with the bone formation inducing properties of pyrrolidones, such as NMP, and optionally biodegradable polymers are utilized in synergistic manner, to treat dental and periodontal diseases, including the integration of dental implants and the filling of tooth sockets following extraction, and to treat orthopedic diseases and failures, in which the enhancement of fracture healing and the augmentation of bone is desired, such as in the alveolar ridge augmentation, in the sinus floor elevation, and in the healing of non-unions, including improvement of the recovery of patients having a surgical bone operation or accidental bone fractures.

SUMMARY OF THE INVENTION

Surprisingly it has now been discovered that administration of the BMPs in combination with pyrrolidones alone or with biodegradable implants, especially membranes, which optionally have been pre-treated with pyrrolidones, such as NMP, enhances bone formation in a synergistic manner to an extent, which could not have been expected on the basis of separate individual bone formation inducing activities of the BMPs or NMP or a combination of NMP and a biodegradable polymer reported in the prior art.

The present invention relates to a pharmaceutical composition comprising at least one bone morphogenetic protein (BMP) and at least one pyrrolidone optionally in a pharmaceutically acceptable carrier, wherein said BMP and said pyrrolidone are present in an amount providing a synergetic therapeutic effect on bone formation.

In one embodiment of the invention the pyrrolidone is N-methyl-2-pyrrolidone (NMP) and the BMP is a recombinant BMP, wherein NMP and said recombinant BMP are present in an amount providing a synergetic therapeutic effect on bone formation.

In another embodiment of the invention the pharmaceutically acceptable carrier is a biodegradable polymer.

In another embodiment of the invention the pharmaceutically acceptable carrier is a biodegradable polymer, which has been pre-treated with the pyrrolidone.

One example of an embodiment of the present invention is a pharmaceutical composition comprising at least one bone morphogenetic protein (BMP), a pyrrolidone and a biodegradable polymer, wherein said BMP, said pyrrolidone and said biodegradable polymer are present in an amount providing a synergetic therapeutic effect on bone formation.

Another example of an embodiment of the present invention is a pharmaceutical composition comprising at least one recombinant bone morphogenetic protein (rBMP), methyl-2-pyrrolidone (NMP) and a biodegradable polymer, which has been pretreated with NMP, wherein said rBMP, said NMP and said pretreated biodegradable polymer are present in an amount providing a synergetic therapeutic effect on bone formation.

The present invention further relates to a method of treating a subject in a need of induction of bone formation, the method comprising simultaneous administration of at least one bone morphogenetic protein (BMP) and at least one pyrrolidone optionally in a pharmaceutically acceptable carrier, wherein said BMP and said pyrrolidone are present in an amount providing a synergetic therapeutic effect on bone formation, to said subject.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 2A: MC3T3-E1 cells treated with increasing amounts of NMP and the maturation determined after 6 days by alkaline phosphatase activity. The maturation of MC3T3-E1 cells increases in a concentration dependent manner with the amount of NMP applied ranging from 0 to 5 Mm of NMP. FIG. 2B: Mineralization by MC3T3-E1 cells seeded on a 6-well plate visualized by Alizarin S-staining. The MC3T3-E1 cells were cultured for 4 weeks in the presence of 5 Mm glycerol phosphate and 1 µg/ml rhBMP-2. In the upper row no NMP was added, in the lower row 2.5 µM NMP was present through out the experiment. The increase of red-stained area in the lower row compared to the upper row shows that maturation determined by mineralization has increased in the presence of 2.5 Mm NMP.

FIG. 4A: Pellets of rhBMP-2 dimers were solubilized for 2 h in phosphate buffered saline supplemented by increasing amounts of different pyrrolidones. (NMP: 1-methyl-2-pyrrolidone; NEP: 1-ethyl-2-pyrrolidone; PB: 2-pyrrolidone; CP: 1-cyclohexyl-2-pyrrolidone). The concentration dependency of pyrrolidones to solubilize rhBMP-2 is shown. In FIG. 4B the influence of NMP, NEP, PB, and CP on MC3T3-E1 cell maturation is shown. The concentration of the four pyrrolidones in the medium was 5 Mm.

DETAILED DESCRIPTION OF THE INVENTION

The present invention is based on the Applicants' further studies to reveal the mechanisms, how pyrrolidones, especially NMP, are capable to enhance bone regeneration. Pyrrolidone-treated membranes, composed of a synthetic biodegradable polymer, namely polylactide/glycolide (PLGA), which membranes are too ridged for use in GBR, show better results in in vivo bone regeneration than untreated or texture like flexible PLGA-membranes, when softened with a plastiziser, N-methyl-2-pyrrolidone (NMP), both in vivo in rabbits and in vitro in a BMP-producing cell line but not in vitro in a non-BMP-producing cell line.

Figure 1:
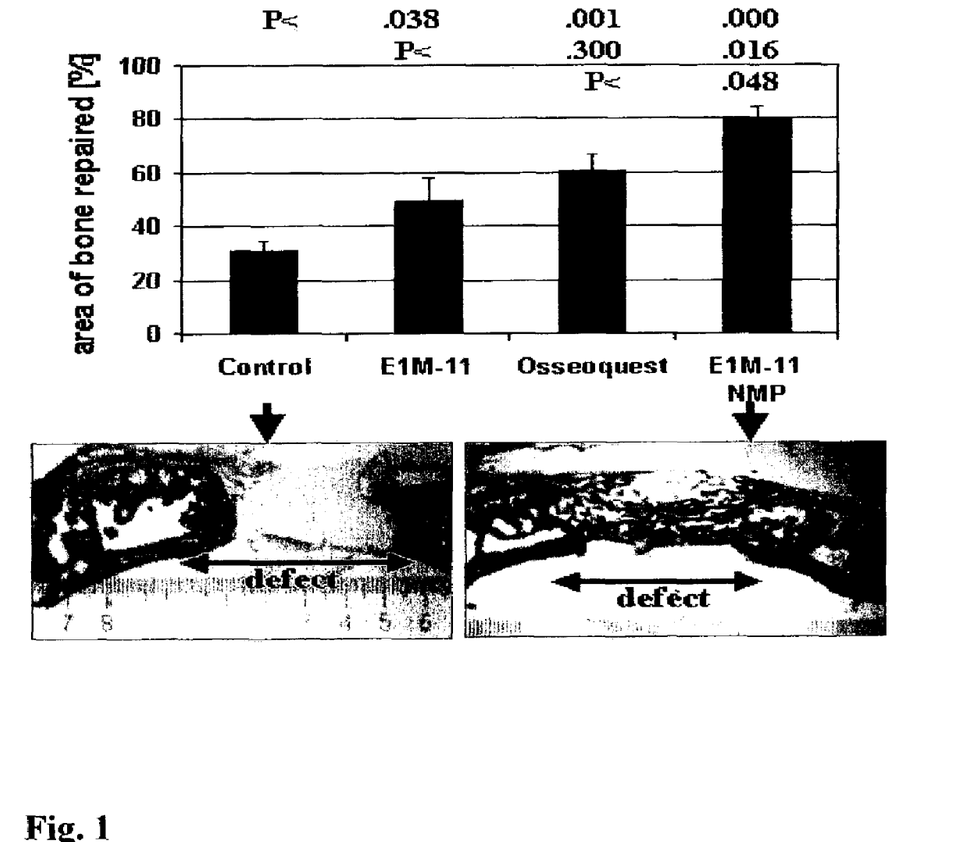
FIG. 1 illustrates the augmentation of bone repair by guided bone regeneration and NMP: 6 mm (in diameter) defects in the calvarial bone were treated by 3 different membranes (E1M-11, OSSEOQUEST™ (synthetic bioabsorbable hydrolyzable polyester) and E1M-11NMP) or left untreated (control). Four weeks after operation the bone regeneration in the defect was determined. The upper panel (FIG. 1A) shows the percentages of the area, where bone regeneration in the defect has occurred in relation to the original defect area. Each value represents the results of eight independent defects. P-values are given. The evaluation was performed with the middle section of the defects stained by Goldner-Trichrome. In the lower panel (FIG. 1B) one example of a control and an E1M-11NMP treated middle section of defects are presented. After Goldner-Trichrome staining bone appears dark green and osteoid red. The extent of the defects is indicated.

The calvarial defect model was chosen as the animal model, because it is the most selective model for bone regeneration due to the poor blood supply and the membranous (cortical) structure of the bone, which has an adverse effect on bone healing. The size of the defect was below the critical size defect and was selected to resemble the typical magnitude of an osteotomy gap in maxillofacial surgery and defects in dentistry [Klinge, B., et al., J Oral Maxillofac Surg 50 (1992) 241–249]. In this animal model three commercial membranes E1M-11 and OSSEOQUEST™ (synthetic bioabsorbable hydrolyzable polyester) and E1M-11 treated with NMP (E1M-11NMP) were tested and they all improve bone regeneration (FIG. 1).

Figure 2:
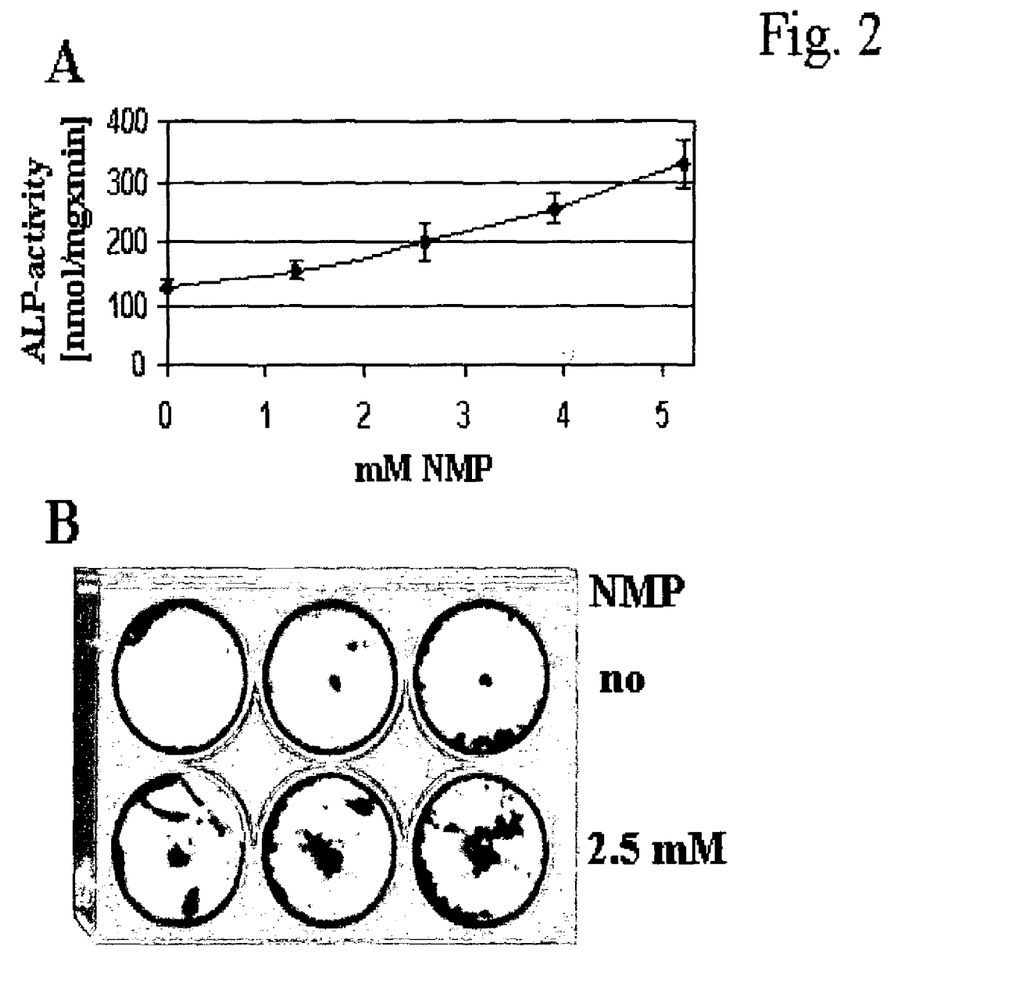
FIG. 2 shows the NMP induced increase of maturation of preosteoblastic cell line (MC3T3-E1) in vitro.

However, the NMP treated membrane performed significantly better and it was concluded that this is due to an increased signal transduction via BMP-receptors. This interpretation was supported by in vitro data derived from a preosteoblastic cell line (MC3T3-E1), where the application of low NMP doses enhanced their maturation (FIG. 2). This cell line is known to secrete BMP, to deposit it in the extracellular matrix and to mature by the action of extracellular BMP acting exclusively on the BMP signal transduction via Smads [Suzawa, M., et al., Endocrin 140 (1999) 2125–2133]. The same signal transduction pathway is also present in C3H10T1/2 cells [Katagiri, T., et al., Biochem Biophys Res Com 172 (1990) 295–300], but no response on NMP application was seen. Therefore NMP's site of action is not at or downstream the BMP receptor level, but NMP acts directly on the extracellular BMP. Thus, the NMP-induced improvement of bone regeneration seen in vivo and accelerated maturation of MC3T3-E1 cells in vitro is due to an NMP mediated increase in the bioactivity/bioavailability of autologous BMPs present in both systems.

In GBR the combination of a synthetic biodegradable polymer membrane, such as a PLGA membrane, treated with NMP expands the function of the membrane from a purely mechanical separator of connective tissue from open space generated for bone in-growth to a delivery device for NMP. By this combination GBR is directly linked to osteoinduction, because the bioactivity/bioavailability of autologous BMP in vivo is increased substantially. To obtain a comparable magnitude of bone regeneration in the same animal model 15 μg of rhBMP-2 are needed (results not shown), which equals the total amount of BMP present in a rabbit (calculated according the BMP content in calves; Reddi et al., 1997, supra).

Therefore the use of NMP in this model is also a good example for enforcing the self-healing process, in this case via autologous BMP.

These results encouraged the Applicants to further studies on the effect of NMP on added BMP, with the expectations that the amount of external BMP needed in the clinical applications could be reduced.

Figure 3:
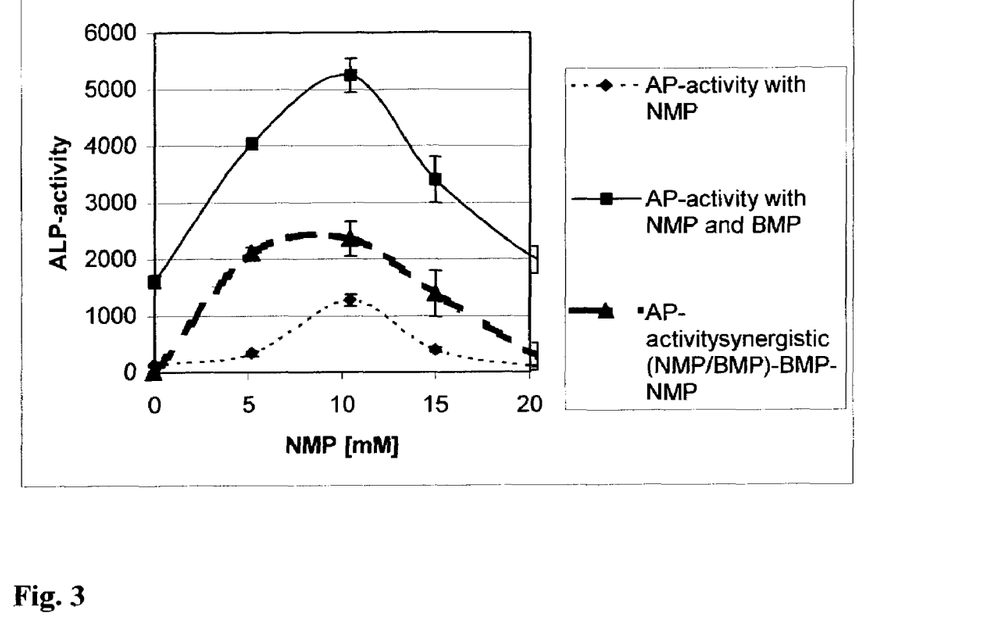
FIG. 3 shows the synergistic effect of NMP and rhBMP-2 on the maturation of MC3T3-E1 cells determined by alkaline phosphatase activity. MC3T3-E1 cells were treated with NMP in the presence or absence of 1 µg rhBMP-2/ml of the medium. For the calculation of the synergistic effect the ALP activity induced by BMP treatment alone and the ALP activity induced by NMP treatment alone was subtracted from the ALP activity achieved in the presence of both BMP and NMP. SD is indicated in the graph.

Surprisingly, however, in further studies it was discovered that an administration of the BMPs in combination with a pyrrolidone, such as NMP, enhances bone formation in a synergistic manner to an unexpected extent, which could not have been foreseen on the basis of separate individual bone formation inducing activities of the BMPs or NMP reported in the prior art (FIG. 3).

This affords advantages in terms of smaller amounts of the material needed for the desired effect, which is of great importance in view of the laborious production of especially the rBMPs. Also, a risk of side effects decreases significantly, when smaller amounts of foreign material can be used. In all, the invention enables for the first time a cost-effective therapeutic utilization of the bone inducing potential of the BMPs, especially the rBMPs.

For the present purposes, the terms BMP or rBMP refer to a member of the BMP family as a dimeric natural or recombinant product, respectively. Thus, for example, the term rBMP covers the members of the BMP subfamily, such as BMP-2 and BMP-4, the members of the OP subfamily, such as OP-1 (or BMP-7) OP-2 (or BMP-8), BMP-5, BMP-6 (or Vgr-1), the members of the CDMP subfamily, such as CDMP-1 (or BMP-14 or GDF-5), the members of the GDF subfamily, such as GDF-1, GDF-3, GDF-8, GDF-9, GDF-11 (or BMP-11), GDF-12 and GDF-14, and the members of other BMP subfamilies, such as BMP-3 (or osteogenin), BMP-9 (or GDF-2), and BMP-10 as well as BMPs 15 and 16, when produced by recombinant technology. Preferred examples of the BMPs and rBMPs useful in the pharmaceutical compositions of the present invention include natural and recombinant BMP-2, BMP-4, BMP-5, BMP-6, and BMP-7, which BMPs at present are known to be critically involved in the formation of new bone. However, the scope of the invention is also intended to cover compositions containing the BMPs, whose role in the bone formation has not so far been clarified.

The natural BMPs useful in the present invention can be obtained for example from human bones as described by Johnson E E, et al. [Clin Orthop 250 (1990) 234–240] or from other mammalian bone sources as easily recognized by those skilled in the art.

The rBMPs useful in the present invention can be prepared by standard recombinant technology using both prokaryotic and eukaryotic expression systems in a conventional manner. In this respect, a reference is made for instance to Cerletti et al. (European Patent Application 0 433 225 A1) and Israel D. I. et al., Growth Factors 7 (1992) 139–150. The production in a prokaryotic expression system, such as in *Escherichia coli* strains or in other suitable bacterial strains, offers advantages in terms of the yield. Prokaryotic expression systems are especially suitable for the production of the rBMP monomers, which then can be dimerized for instance as described by Cerletti et al. (supra). On the other hand, eukaryotic expression systems, such as mammalian or insect cells, especially mammalian cells, and especially those using a protein-free medium, are advantageous in terms of the product safety. Examples of suitable mammalian cells include Chinese hamster ovarian (CHO) cells. Mammalian expression systems are especially preferable for the production of the rBMPs. However, the choice of a suitable production system is well within the knowledge of a man skilled in the art.

The pyrrolidones useful in the pharmaceutical compositions of present invention are any pyrrolidone known in the art of chemistry to have a plastizising or solubilizing properties without having a tissue impairing effects or toxic effects. Such pyrrolidones include, for example, alkyl- or cycloalkyl-substituted pyrrolidones, such as 1-methyl-2-pyrrolidone (NMP), 1-ethyl-2-pyrrolidone (NEP), 2-pyrrolidone (PB), and 1-cyclohexyl-2-pyrrolidone (CP), with NMP and NEP being preferred examples. Additionally, pyrrolidone-based polymers, such polyvinylpyrrolidones, may also be useful in the pharmaceutical compositions of the invention.

The pharmaceutical composition of the invention may contain a pharmaceutically acceptable carrier. The carrier may be any suitable liquid, solid or semisolid carrier, including water, saline, buffers, such as phosphate, acetate, citrate, tartate and similar buffers, to form a solution or a suspension, and a natural or synthetic biodegradable polymer or copolymer. Due to the solubilizing properties of the pyrrolidone component of the composition, additional adjuvants are usually not necessary for improving the solubility of the BMP component. However, the liquid carrier may contain adjuvants normally used for preparation of pharmaceutical solutions and suspensions, such as co-solvents, detergents, stabilizers, antioxidants, viscosity improving agents, preservatives, and like. Where necessary, the composition may be sterilized with any suitable sterilization method, such membrane filtration.

In one preferred embodiment of the invention the pharmaceutically acceptable carrier is a slow release system based on synthetic biogradable polymers, such as polyglycolide, polylactides, polycaprolactones, polytrimethylenecarbonates, polyhydroxybutyrates, polyhydroxyvalerates, polydioxanones, polyorthoesters, polycarbonates, polytyrosinecarbonates, polyorthocarbonates, polyalkylene oxalates, polyalkylene succinates, poly(malic acid), poly(maleic anhydride), polypeptides, polydepsipeptides, polyvinylalcohol, polyesteramides, polyamides, polyanhydrides, polyurethanes, polyphosphazenes, polycyanoacrylates, polyfumarates, poly(amino acids), modified polysaccharides (like cellulose, starch, dextran, chitin, chitosan, etc.), modified proteins (like collagen, casein, fibrin, etc.) and their copolymers, terpolymers or combinations or mixtures or polymer blends thereof. Polyglycolide, poly(L-lactide-co-glycolide), poly(D,L-lactide-co-glycolide), poly(L-lactide), poly(D,L-lactide), poly(L-lactide-co-D,L-lactide), polycaprolactone, poly(L-lactide-co-caprolactone), poly(D,L-lactide-co-caprolactone) polytrimethylenecarbonate, poly(L-lactide-co-trimethylenecarbonate), poly(D,L-lactide-co-trimethylenecarbonate), polydioxanone and copolymers, terpolymers and polymer blends thereof are highly preferred examples of polymers. Most preferably, the copolymer of polylactide with glycolides, such as poly-DL-lactide-co-glycolide (PLGA), is used as a carrier.

Other examples of pharmaceutically acceptable carriers useful in the present invention include proteins, like collagen and fibrin, calcium phosphates (tri-calciumphospates, hydroxyapatite), bone cements, bioglass, coral minerals (Algipore®), nacre, egg shell, bovine derived hydroxyapatite (Bio-Oss®), and all osteoconductive (porous) materials.

The pharmaceutical composition of the invention may be formulated in any suitable way applicable for simultaneously administering the BMP component(s) and the pyrrolidone component(s). In one embodiment, the pharmaceutical composition of the invention can be prepared by mixing suitable bone formation inducing amounts of the BMP and the pyrrolidone component(s) and optionally the pharmaceutically acceptable carrier.

Alternatively, in another embodiment of the invention a biodegradable polymer, preferably in a form of a membrane, is used as pretreated with a pyrrolidone. The treatment comprises simply immersing the molded polymer in a solution containing the desired pyrrolidone for a period of time needed for softening the polymer, such as for 15 sec to 3 minutes, or to achieve a constant concentration of the pyrrolidone in the polymer and then air-drying. Then the BMP can be introduced by heparinization [Ruppert, R. et al. Eur J Biochem 237 (1996) 295–302] of the carrier membrane. The polymer should remain flexible long enough for the insertion of the implant. Alternatively, the molded polymer is similarly pretreated with a mixture of pyrrolidone and the BMP, whereby the BMP attaches to the polymer by simple absorption. Alternatively, the BMP can be applied separately but simultaneously in a different carrier, such as fibrin, collagen, polyethyleneglycol, bioclass, hydroxyapatites, calcium phosphatates and similar carrier material, such as those listed above.

In one embodiment of the invention the pharmaceutical composition is in a form of an implant, including membranes, films, plates, mesh plates, screws tabs and other formed bodies.

The pharmaceutical compositions of the invention contain a bone formation inducing amount of at least one BMP or rBMP and a bone formation inducing amount of at least one pyrrolidone. Such an amount may be for example from about 0.001 to about 4 mg of the BMP(s) or rBMP(s) and from about 0.005 to about 50 percent by weight of the pyrrolidone(s) per dose. However, the bone formation inducing amounts may vary in different applications, especially in the case of the BMP. Thus, smaller amounts may be sufficient in, for instance dental applications whereas somewhat larger amounts may be needed for the desired effect in, for instance, unilateral and multilateral spinal fusions, treatments of non-unions, treatments of osteoporosis, and in-growth of (hip) implants.

The dosage of the compositions of the invention depends on the individual patients and the disorder to be treated. An exemplary single dose of a composition of the invention is within the range of about 0.001 to about 4 mg. However, a smaller dose may be sufficient in, for instance in the treatment of dental patients, whereas somewhat larger doses may be needed for the desired effect in other treatments.

The therapeutic method of the invention is based on the simultaneous use of at least one bone morphogenetic protein (BMP) and a bone formation-inducing amount of at least one pyrrolidone, whereby a synergetic effect is achieved. In the method of the invention a subject in a need of induction of bone formation is simultaneously administered a bone formation-inducing amount of at least one bone morphogenetic protein (BMP) and a bone formation-inducing amount of at least one pyrrolidone optionally in a pharmaceutically acceptable carrier, wherein said BMP(s) and said pyrrolidone(s) are administered in an amount providing a synergetic therapeutic effect on bone formation. For the purposes of the method of the invention, the expression "simultaneously administering" includes both simultaneous and sequential administering. Thus, in one embodiment of the method of the invention the BMP component(s) and the pyrrolidone component(s) may be administered in a form of a pharmaceutical composition of the invention. In another embodiment of the method of the invention, the BMP(s) may be administered sequentially introducing a pharmaceutically acceptable carrier pretreated with a pyrrolidone, such as NMP, to the site of the treatment and then applying a suitable synergistic amount of the BMP.

The amounts of the BMP component(s) and the pyrrolidone component(s) used in the method vary depending on the condition to be treated and will be decided by the treating physician. Exemplary doses are as given above.

The invention is illustrated by the following examples, which are given only for illustrative purposes.

For statistical analysis, unpaired Students T-test was implemented by a commercially available software package (SSPE, Chicago, Ill.). All values are represented as mean±standard error of the mean.

Analysis of Data

The digital image of the vertical section from the middle of the defect was taken with a scale (mm) in order to localize the defect margins, which were 6 mm apart. In combination with the calvarial bone thickness of the surrounding bone the total area of the defect could be reconstructed. Using the Adobe Photoshop 5.0 program the total pixel number of the defect area could be determined. The part of the total defect filled by bone was also determined and expressed by the pixel number of the bony area. Percentage of bone healing was calculated as follows:

Bone healing [%]=pixel number of the bone area×100/ total pixel number of defect.

Cell culture technique and alkaline phosphatase determination.

MC3T3-E1 cells were grown in an alpha-modified Minimum Essential Medium (Life Technologies, Inc., Grand Island, N.Y.) containing 10% fetal calf serum (Life Technologies, Inc.), 50 µg/ml gentamycin, and 50 µg/ml ascorbic acid. C3H10T1/2 cells were grown in basal medium Eagle, and 50 µg/ml gentamycin. To examine the action of NMP on both cell lines, $1 \times 10^5$ cells per well were plated in 6-well plates and NMP subsequently added. Medium exchange was performed after 3 days and alkaline phosphatase (ALP) was determined according to Lowry, O. et al. [J. Biol. Chem. 207 (1954) 19–37]: p-nitrophenol liberated was converted to p-nitrophenylate by adding 400 µl of 1 M NaOH, which was quantitated by measuring the absorbance at 410 nm (epsilon=17500/molxcm). Alkaline phosphatase activity was normalized to total protein and expressed as nmol nitrophenylate generated per min per mg protein.

Mineralization was determined in MC3T3-E1 cells grown in the same medium supplemented with 5 mM glycerol phosphate and 1 µg/ml rhBMP-2. Alizarin red-S staining was performed after 4 weeks according to Bodine, P. V. N., et al. [J Bone Mineral Res 11 (1996) 806–819].

EXAMPLE 1

Effect of NMP-treated PLGA Membranes on Bone Regeneration

To evaluate the bone regeneration, standardized defects were generated in the calvarial bone of rabbits. New Zealand white rabbits (3.5–4.0 kg) were treated according to the guidelines of the local authorities. The protocol for these studies was approved and controlled by the kantonalem Verterinäramt, Zurich. After sedation four 6 mm craniotomy defects were created with a 6 mm trephine in a dental hand piece. To seal the defects from the dural side 6.1 mm in diameter membrane was poked through the calvarial bone. This membrane was fixed by the pressure from the dura. Another rectangular membrane of 10×10 mm was placed above the defect. The four membranes of the top were sutured together and the entire unit sutured to the lateral remaining periost. After four weeks the animals were sacrificed, the calvarial bone excised, radiographed, embedded in methacrylate and stained by Goldner-Trichrome staining as described Weber, F. E., et al. [Biochem. Biophys. Res. Commun. 286 (2001) 554–558].

Three different membranes all consisting of PLGA were tested: OSSEOQUEST™ (synthetic bioabsorbable hydrolyzable polyester) (Gore-Tex®, USA), E1M-11 (Inion OY, Finland), and E1M-11 membrane treated with NMP (E1M-11 NMP). NMP treatment involves the dipping of the membrane in NMP for 30 seconds followed by air-drying for 15 minutes. Osteoinductive rhBMP-2 was produced as described Weber, F. E., et al., 2001, supra.

The evaluation of bone regeneration in standardized defects generated in the calvarial bone of rabbits showed that all 3 membranes improved bone healing significantly compared to untreated control defects (FIG. 1). With a bony healing of 79.06±5.6% of the defect the NMP treated E1M-11NMP membrane was the most effective.

The reason for this significant improved bone regeneration compared to the other two membranes could not be attributed to the softening effect of NMP to the E1M-11 membrane alone, because also the reference membrane OSSEOQUEST™ (synthetic bioabsorbable hydrolyzable polyester) is soft and flexible due to its texture like structure. Therefore additional experiments were performed with the configuration of two untreated control defects located next to two E1M-11NMP treated defects. Due to the presence of NMP applied by membranes close to these untreated defects they were named pseudo-control defects. The results showed that pseudo-control defects healed significantly better than true control defects (pseudo-control 60.05±5.4%; control 30.3±4.1% healing; P<0.038). Therefore all in vivo data suggested a positive effect on bone healing by NMP.

EXAMPLE 2

The Synergistic Effect of NMP-treated PLGA Membranes and rhBMP-2 on Bone Regeneration Together First, to verify the osteoinductive activity of NMP an embryonic, murine, mesenchymal stem cell line C3H10T1/2 and a preosteoblastic cell line MC3T3-E1 were used and cultured as described above. C3H10T1/2 cells can differentiate into cartilage, bone or adipose cells, whereas MC3T3-E1 produces and releases autologous BMP. Alkaline phosphatase activity was used as a marker for the differentiation into the osteoblastic lineage.

As illustrated in FIG. 2, low doses of NMP increased the alkaline phosphatase activity by a factor of 2.5–3.0 and accelerated the maturation of preosteoblasts to osteoblasts in MC3T3-E1. This acceleration of maturation also continued for a long period of time, because the NMP-treatment of MC3T3-E1 cells increased mineralisation performed by mature osteoblasts as determined by alizarin-S-staining (FIG. 2B). On the other hand, the alkaline phosphatase activity of C3H10T1/2 cells treated with up to 5 mM NMP was not increased (data not shown). Thus NMP alone is not osteoinductive.

Since the major difference between the cell lines is the presence of BMP, which is only produced by the MC3T3-E1 cells, the effect of external BMP was studied in the same test system using MC3T3-E1 cells. Specifically, cells were plated at day one in 4 ml medium and ALP determination is performed on day 6. On day 1 BMP was added to the cells from a stock solution of 2 mg/ml rhBMP-2 (set forth in SEQ ID NO:1) in 1 mM HCl to a concentration of 1 µg/ml. NMP was added to the cells at the same time point as a undiluted liquid to a concentration of 0.1–20 mM. After application the NMP and rhBMP was mixed by gently swirling the entire 6 well plate. In a separate experiment, the cells were treated with NMP only. For the calculation of the synergistic effect, the ALP activity induced by rhBMP treatment alone and the ALP activity induced by NMP treatment alone was subtracted from the ALP activity achieved in the presence of both rhBMP and NMP. The results are shown in FIG. 3.

EXAMPLE 3

Interaction of Different Pyrrolidones with rhBMP-2

Because NMP is known to be a good solvent for a variety of organic and inorganic substances, it was speculated and analyzed whether the observed synergistic effect of a NMP and BMP could be due to a solubilizing effect of NMP on rhBMP. Two to twenty micrograms of the rhBMP protein was lyophilized in a speed-vac to form a solid rhBMP disc. 50 μl of phosphate buffered saline with an increasing amount of 1-methyl-2-pyrrolidone (NMP), 1-ethyl-2-pyrrolidone (NEP), 2-pyrrolidone (PB), and 1-cyclohexyl-2-pyrrolidone (CP) were added, mixed and solved under agitation. After 2 h the protein in the remaining disc was sedimented (22,000× g, 30 min) and the protein content of 20 μl from the supernatant determined by a slot-blot method (Weber, F. E., et al., 2002, supra).

Figure 4:
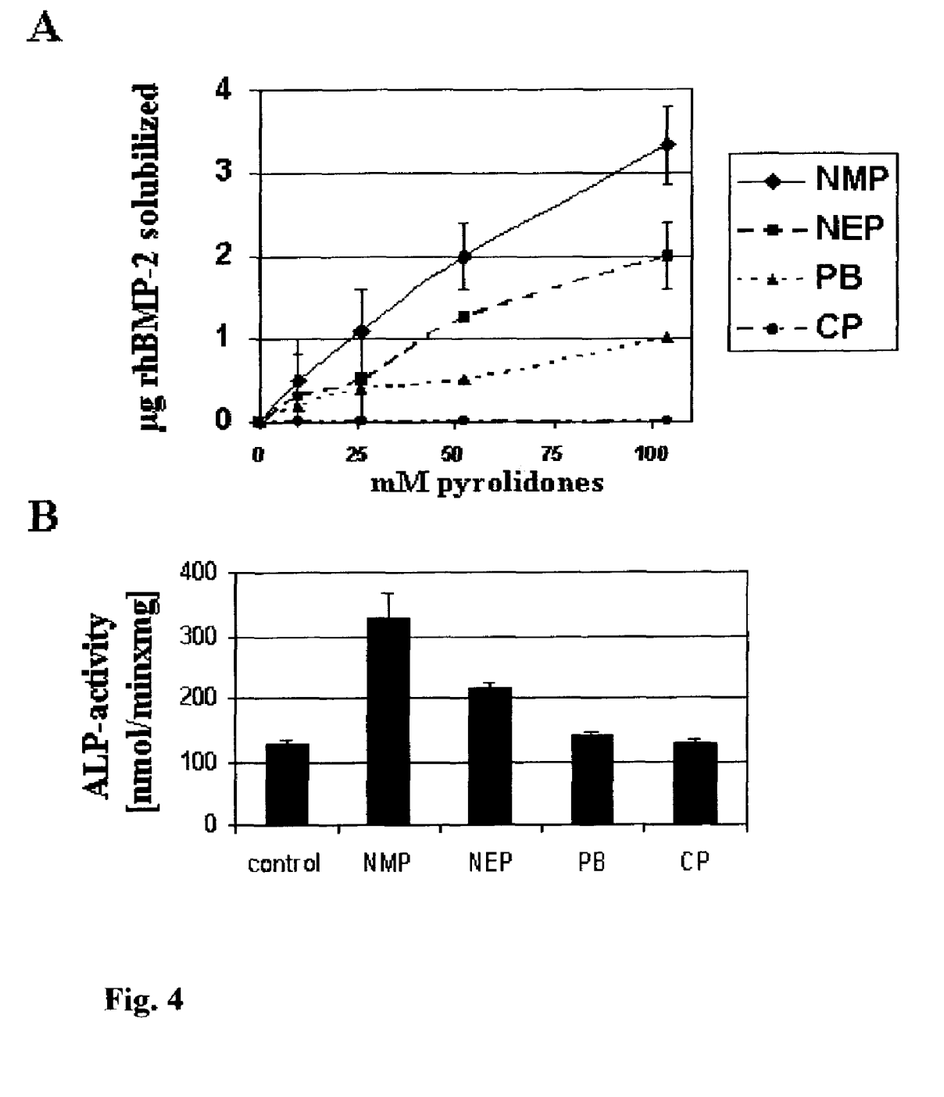
FIG. 4 shows the correlation between the potential of different pyrrolidones to solubilize rhBMP-2 dimers and the effect of the same substances on the maturation of a preosteoblastic cell line (MC3T3-E1).

As can be seen in FIG. 4, pyrrolidone concentrations of the same range as used in the in vitro study described in Example 2 with NMP are sufficient to solubilize otherwise insoluble rhBMP. The results illustrated in FIG. 4A allow the grading of the different pyrrolidones for their potential to solubilize rhBMP-2 in a declining order: 1-methyl-2-pyrrolidone (NMP)>1-ethyl-2-pyrrolidone (NEP)>2-pyrrolidone (PB)>1-cyclohexyl-2-pyrrolidone (CP).

When the same pyrrolidones were tested in MC3T3-E1 cells as described in Example 2, the increase in alkaline phosphatase activity followed the same ranking (FIG. 4B). Therefore the potential of the pyrrolidones to solubilize rhBMP is in a direct relation to the effect of the pyrrolidones on MC3T3-E1 cell maturation.

The effect of pure NMP on a preosteoblastic cell line (MC3T3-E1) was studied. The results showed that NMP in low doses accelerates the maturation of preosteoblasts to osteoblasts most likely by increasing the bioactivity/availability of autologous bone morphogenetic protein (BMP) due to its binding and solubilizing capabilities for BMPs. Therefore NMP or other pyrrolidones can be used in medicine to increase the bioactivity of autologous proteins and to apply recombinant proteins of low solubility. In addition we extended the function of the GBR membrane from a mechanical separator of tissues to a delivery device for a bioactive substance.

The invention claimed is:

1. A pharmaceutical composition comprising a bone morphogenetic protein and a pyrrolidone in a pharmaceutically acceptable carrier, wherein said bone morphogenetic protein and said pyrrolidone are present in an amount at or adjacent to a site of administration of the pharmaceutical composition and at the time of administration sufficient to provide a synergistic therapeutic effect on bone formation, wherein said bone morphogenetic protein is selected from the group consisting of BMP-2, BMP-4, BMP-5, BMP-6 and BMP-7, and wherein said pyrrolidone is selected from the group consisting of 1-methyl-2-pyrrolidone, 1-ethyl-2-pyrrolidone, 2-pyrrolidone and 1-cyclohexyl-2-pyrrolidone.

2. The pharmaceutical composition of claim 1, wherein the pyrrolidone is N-methyl-2-pyrrolidone.

3. The pharmaceutical composition of claim 1, wherein the bone morphogenetic protein is a recombinant bone morphogenetic protein.

4. The pharmaceutical composition of claim 3, wherein the recombinant bone morphogenetic protein is rBMP-2 and/or rBMP-4.

5. The pharmaceutical composition of claim 1, wherein the pyrrolidone is N-methyl-2-pyrrolidone and the bone morphogenetic protein is rBMP-2 or rBMP-4.

6. The pharmaceutical composition of claim 1, wherein the pharmaceutically acceptable carrier is a biodegradable polymer.

7. The pharmaceutical composition of claim 6, wherein said biodegradable polymer is present as a single polymer, copolymer, terpolymer, or polymer blend, and is selected from the group consisting of polyglycolide, polylactides, polycaprolactones, polytrimethylenecarbonates, polyhydroxybutyrates, polyhydroxyvalerates, polydioxanones, polyorthoesters, polycarbonates, polytyrosinecarbonates, polyorthocarbonates, polyalkylene oxalates, polyalkylene succinates, poly(malic acid), poly(maleic anhydride), polypeptides, polydepsipeptides, polyvinylalcohol, polyesteramides, polyamides, polyanhydrides, polyurethanes, polyphosphazenes, polycyanoacrylates, polyfumarates, poly(amino acids), modified polysaccharides, and modified proteins.

8. The pharmaceutical composition of claim 6, wherein the biodegradable polymer is present as a single polymer, copolymer, terpolymer, or polymer blend, and is selected from the group consisting of polyglycolide, poly(L-lactide-co-glycolide), poly(D,L-lactide-co-glycolide), poly(L-lactide), poly(D,L-lactide), poly(L-lactide-co-D,L-lactide), polycaprolactone, poly(L-lactide-co-caprolactone), poly(D,L-lactide-co-caprolactone) polytrimethylenecarbonate, poly(L-lactide-co-trimethylenecarbonate), poly(D,L-lactide-co-trimethylenecarbonate), and polydioxanone.

9. The pharmaceutical composition of claim 8, wherein the biodegradable polymer is a poly-DL-lactide-co-glycolide.

10. A pharmaceutical composition comprising a bone morphogenetic protein and a pyrrolidone in a biodegradable polymer, wherein said bone morphogenetic protein, said pyrrolidone and said biodegradable polymer are present in an amount at or adjacent to a site of administration of the pharmaceutical composition and at the time of administration sufficient to provide a synergistic therapeutic effect on bone formation, wherein said bone morphogenetic protein is selected from the group consisting of BMP-2, BMP-4, BMP-5, BMP-6 and BMP-7, and wherein said pyrrolidone is selected from the group consisting of 1-methyl-2-pyrrolidone, 1-ethyl-2-pyrrolidone, 2-pyrrolidone and 1-cyclohexyl-2-pyrrolidone.

11. The pharmaceutical composition of claim 10, wherein said bone morphogenetic protein is a recombinant bone morphogenetic protein, said pyrrolidone is N-methyl-2-pyrrolidone, and said biodegradable polymer is a poly-DL-lactide-co-glycolide, and wherein said recombinant bone morphogenetic protein, said N-methyl-2-pyrrolidone, and said poly-DL-lactide-co-glycolide are present in an amount sufficient to provide a synergetic therapeutic effect on bone formation.

12. A method of treating a subject in a need of induction of bone formation comprising administering to said subject a bone formation-inducing amount of a bone morphogenetic protein, and a bone formation-inducing amount of a pyrrolidone optionally in a pharmaceutically acceptable carrier, wherein said bone morphogenetic protein and said pyrrolidone are administered in an amount at or adjacent to a site of administration of the pharmaceutical composition and at the time of administration sufficient to provide a synergistic therapeutic effect on bone formation, wherein said bone morphogenetic protein is selected from the group consisting of BMP-2, BMP-4, BMP-5, BMP-6 and BMP-7, and wherein said pyrrolidone is selected from the group consisting of 1-methyl-2-pyrrolidone, 1-ethyl-2-pyrrolidone, 2-pyrrolidone and 1-cyclohexyl-2-pyrrolidone.

13. The method of claim 12, wherein said bone morphogenetic protein and said pyrrolidone optionally in a pharmaceutically acceptable carrier are simultaneously administered in a pharmaceutical composition in an amount sufficient to provide a synergetic therapeutic effect on bone formation.

14. The method of claim 13, wherein said pyrrolidone is selected from the group consisting of from pyrrolidones, pyrrolidones optionally substituted with alkyl or cycloalkyl groups; and said pharmaceutically acceptable carrier is a biodegradable polymer.

15. The method of claim 14, wherein said pharmaceutically acceptable carrier is present as a single polymer, copolymer, terpolymer, or polymer blend and is selected from the group consisting of polyglycolide, poly(L-lactide-co-glycolide), poly(D,L-lactide-co-glycolide), poly(L-lactide), poly(D,L-lactide), poly(L-lactide-co-D,L-lactide), polycaprolactone, poly(L-lactide-co-caprolactone), poly(D,L-lactide-co-caprolactone) polytrimethylenecarbonate, poly(L-lactide-co-trimethylenecarbonate), poly(D,L-lactide-co-trimethylenecarbonate), and polydioxanone.

16. The method of claim 14, wherein said pyrrolidone is 1-methyl-2-pyrrolidone, said bone morphogenetic protein is rBMP-2 or rBMP-4, and said pharmaceutically acceptable carrier is a poly-DL-lactide-co-glycolide.

17. The pharmaceutical composition of claim 1, wherein the pyrrolidone is present at a concentration of between about 0.1 mM and 20 mM.

18. The pharmaceutical composition of claim 1, wherein the pyrrolidone is present at a concentration of between about 0.1 mM and 10 mM.

19. The pharmaceutical composition of claim 1, wherein the pyrrolidone is present at a concentration of between about 0.1 mM and 5 mM.

20. The pharmaceutical composition of claim 10, wherein the pyrrolidone is present at a concentration of between about 0.1 mM and 20 mM.

21. The pharmaceutical composition of claim 10, wherein the pyrrolidone is present at a concentration of between about 0.1 mM and 10 mM.

22. The pharmaceutical composition of claim 10, wherein the pyrrolidone is present at a concentration of between about 0.1 mM and 5 mM.

23. The method of claim 12, wherein the pyrrolidone is present at a concentration of between about 0.1 mM and 20 mM.

24. The method of claim 12, wherein the pyrrolidone is present at a concentration of between about 0.1 mM and 10 mM.

25. The method of claim 12, wherein the pyrrolidone is present at a concentration of between about 0.1 mM and 5 mM.

* * * * *